US009173603B2

(12) United States Patent
Molcho et al.

(10) Patent No.: US 9,173,603 B2
(45) Date of Patent: Nov. 3, 2015

(54) NON-INVASIVE DEVICE AND METHOD FOR MEASURING BILIRUBIN LEVELS

(76) Inventors: Jonathan Molcho, Omer (IL); Ehud Zmora, Beer Sheva (IL)

(*) Notice: Subject to any disclaimer, the term of this patent is extended or adjusted under 35 U.S.C. 154(b) by 590 days.

(21) Appl. No.: 13/551,862

(22) Filed: Jul. 18, 2012

(65) Prior Publication Data
US 2013/0023742 A1    Jan. 24, 2013

Related U.S. Application Data

(60) Provisional application No. 61/509,608, filed on Jul. 20, 2011.

(51) Int. Cl.
*A61B 5/1455*  (2006.01)
*A61B 5/00*  (2006.01)

(52) U.S. Cl.
CPC ............ *A61B 5/1455* (2013.01); *A61B 5/14557* (2013.01); *A61B 5/443* (2013.01)

(58) Field of Classification Search
CPC ..... A61B 5/1455; A61B 5/0059; A61B 5/443
See application file for complete search history.

(56) References Cited

U.S. PATENT DOCUMENTS

| 4,267,844 | A | | 5/1981 | Yamanashi |
| 5,259,382 | A | * | 11/1993 | Kronberg ...................... 600/315 |
| 6,195,574 | B1 | | 2/2001 | Kumar |
| 6,615,064 | B1 | * | 9/2003 | Aldrich ........................ 600/316 |
| 2003/0011773 | A1 | | 1/2003 | Dick |

FOREIGN PATENT DOCUMENTS

WO    WO 96/39927    12/1996

* cited by examiner

*Primary Examiner* — Eric Winakur
(74) *Attorney, Agent, or Firm* — Henry M. Sinai; IP-Partnership

(57) ABSTRACT

A transcutaneous non-invasive device and method for measuring bilirubin levels is provided. The device and method utilize optical, electrical, and mechanical means in communication with processing means to calculate the serum bilirubin concentration. Blanching pressure is applied to the tissue, whose thickness is measured. The level of bilirubin is calculated from the thickness of the tissue and the detected and measured values of radiation transmitted through the living tissue.

22 Claims, 5 Drawing Sheets

NON-INVASIVE DEVICE AND METHOD FOR MEASURING BILIRUBIN LEVELS

CROSS-REFERENCE TO RELATED APPLICATIONS

This application claims the benefit of US provisional patent application No. 61/509,608 filed on Jul. 20, 2011 and incorporated by reference as if set forth herein.

FIELD OF THE INVENTION

The present invention relates to medical devices for measuring bilirubin levels in a living tissue. More particularly, the present invention relates to a non-invasive device and method for estimating bilirubin levels in a newborn subject for diagnosing jaundice.

BACKGROUND OF THE INVENTION

Jaundice is fairly common among newborn infants, and is presumably a consequence of metabolic and physiological adjustments after birth. Often, the jaundice disappears within a fairly short period of time. In many cases the jaundice is detected early and treated effectively thus curing the infant within a fairly short period of time. When an infant is jaundiced the serum bilirubin normally rises to a high level. In extreme cases, a brain-damaging condition known as kernicterus can occur, leading to significant lifelong disability. In other extreme cases the jaundice can progress severely and even lead to death. Jaundice is usually diagnosed by an invasive blood test in which blood sample is usually taken from the heel. While this blood test is considered to be safe, obtaining the blood sample is an uncomfortable invasive procedure for a newborn infant.

U.S. Pat. No. 4,267,844 by Yamanishi relates to an electro-optical medical instrument provided for measuring non-invasively the presence of bilirubin in skin tissue. The instrument in this publication utilizes a source of flash light and optical means to provide a beam of light to illuminate the skin tissue. A portion of the reflected light is collected and separated by optical means to two components: One, having a central wavelength of 455 nm, which is known as being highly absorbed by bilirubin in skin tissue; And another having a wavelength greater than 500 nm, which absorption by the bilirubin in the skin tissue is low. These optical signals are measured by photoelectric transducers, the electrical output of which is amplified, and then used to compute a bilirubin indication by means of a logarithmic converter. User obtained calibration is called upon to convert the bilirubin indication to serum bilirubin concentration.

U.S. Pat. No. 6,064,898 by Aldrich relates to a non-invasive blood component analyzer using spectrophotometry. The analyzer in this publication utilizes measurements of transmitted light having various wavelengths selected in accordance with the blood components of interest. The parameters used to derive the blood components are each given by the difference between the systolic and diastolic values of the relevant measured signal. The visible wavelengths mentioned are 420 nm, 548 nm, 506 nm, 521 nm, 569 nm, and 586 nm. The first two are proposed for the measurement of bilirubin concentration in skin tissue.

Another non-invasive bilirubin measuring instrument is described in U.S. Pat. No. 5,792,049, by Eppstein, in which the reflectance of skin tissue is measured at several visible and near infra-red wavelengths. The measured values of reflectance are utilized to arrive at an estimate of the serum bilirubin concentration. For calibrating the instrument, the reflectance of a calibration target is measured at these same wavelengths It is an object of the present invention to provide a method and means for applying non-invasive measurements for detecting the bilirubin level in a subject. It is a further object of the present invention to provide a method and means for applying non-invasive measurements for detecting the bilirubin level in a subject in a fast and simple manner.

Other objects and advantages of the present invention will become apparent as the description proceeds.

BRIEF DESCRIPTION OF THE DRAWINGS

The present invention is illustrated by way of example in the accompanying drawings, in which similar references consistently indicate similar elements and in which:

FIGS. 3A to 3C schematically illustrate one embodiment of the invention for operating the device of the invention utilizing a synchronous detection approach, wherein FIG. 3A shows an illustration of the measurement setup, FIG. 3B shows an illustration of an embodiment of a radiation source, and FIG. 3C shows an illustration of an embodiment of a synchronous detector;

FIGS. 4A and 4B schematically illustrate another embodiment of the invention utilizing flashtube as a light source, wherein FIG. 4A shows a possible measurement setup and FIG. 4B shows a possible embodiment of a detection unit; and FIGS. 5A and 5B schematically illustrate a device for measuring bilirubin levels according to yet another embodiment of the invention, wherein FIG. 5A shows a perspective view of the device and FIG. 5B shows a rear view of the device.

Figure 1:
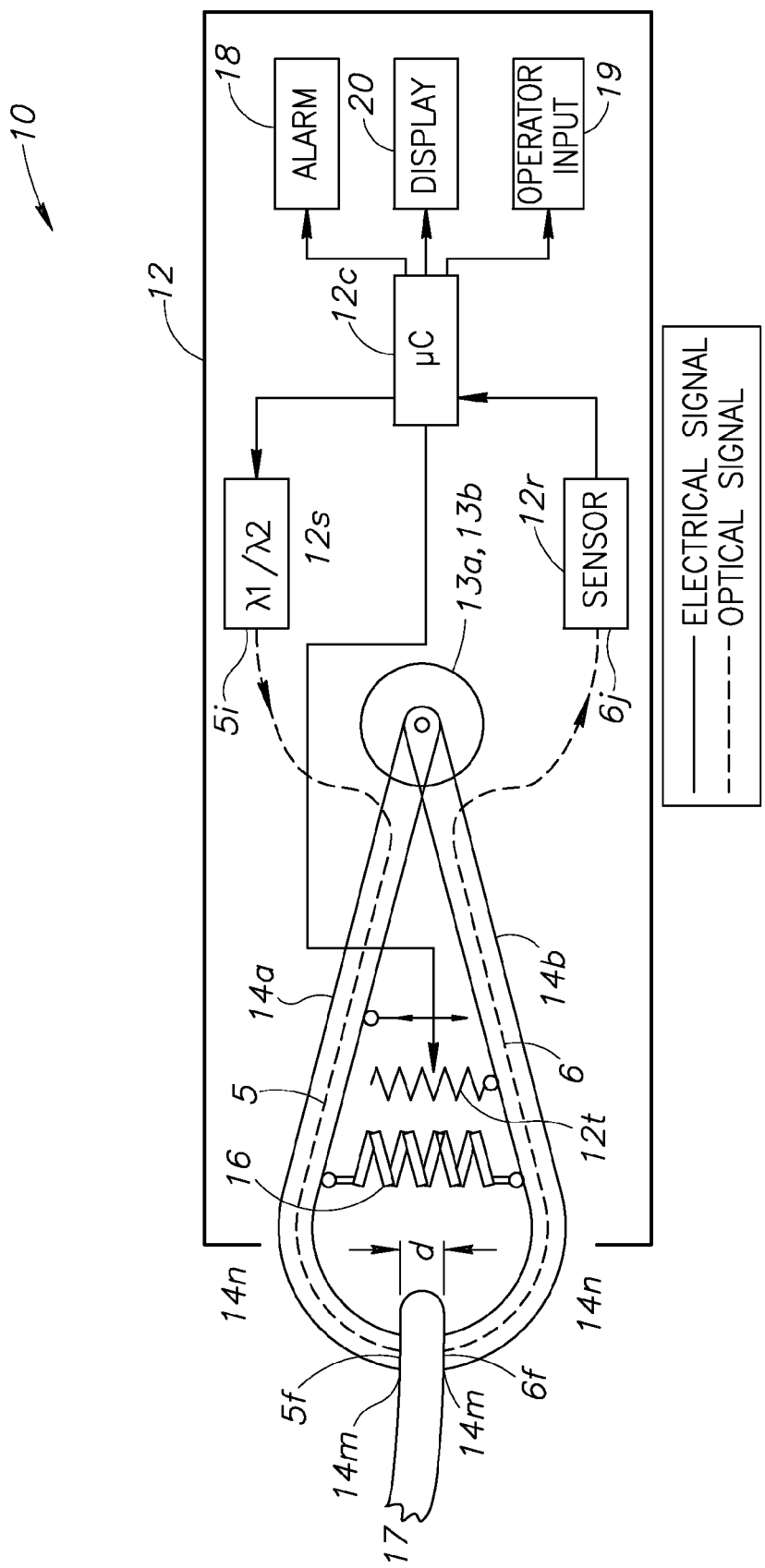
FIG. 1 schematically illustrates a device for measuring bilirubin levels according to one general embodiment of the present invention.

It is noted that the embodiments exemplified in the figures are not intended to be in scale and are in diagram form to facilitate ease of understanding and description.

SUMMARY OF THE INVENTION

The present invention presents a system and device for non-invasive measurement of bilirubin levels by transmitting radiation through a subject's living tissue. Blanching pressure is applied to the tissue and the thickness of the tissue is also measured.

In an embodiment of the present invention, there is provided a non-invasive device for measuring the bilirubin level of a subject. The device includes at least one radiation source for radiating a subject's living tissue, at least one detector for detecting rays transmitted through the tissue, means for applying blanching pressure to the portion of the subject's living tissue; means for measuring the thickness of the portion of the subject's living tissue through which radiation is being transmitted and processing means connected to the radiation source, the detector and the thickness measuring means. The radiation source is configured to emit radiation in at least two wavelengths. The processing means are configured to calculate the bilirubin level of the subject using data obtained from the detector and from the thickness measuring means.

Furthermore in accordance with an embodiment of the invention, the means for applying blanching pressure comprise one of group of devices including a pair of rotatable arms, a single moving or rotating arm and a clip or pincer device, configured to be attached to the tissue being measured.

Furthermore in accordance with an embodiment of the invention, the wavelengths may comprise a first wavelength ($\lambda 1$) within a range 520 nm±5 nm and a second wavelength ($\lambda 2$) within a range 470 nm±10 nm.

Furthermore in accordance with an embodiment of the invention, the radiation source includes one of a group including at least two laser diodes, at least two light emitting diodes (LEDs), and at least one laser diode together with at least one LED. Alternatively, the radiation source may include a white light emitter and two filters for filtering the emitted white light.

Furthermore in accordance with an embodiment of the invention, the device further includes optical means configured to direct beams of light emitted from the at least one radiation source towards the subject's living tissue.

Furthermore in accordance with an embodiment of the invention, the device further includes light guiding means and optical coupling means, where the optical coupling means configured to direct beams of light received from the light guiding means to the detector.

Furthermore in accordance with an embodiment of the invention, the light beams are transmitted through the tissue at different times.

Furthermore in accordance with an embodiment of the invention, the radiation source includes means for emitting a synchronous signal. The synchronous signal may include first and second oscillators, configured to generate first and second electrical signals having first and second frequencies, respectively; first and second driver units electrically coupled to the first and second oscillators; first and second light emitting elements adapted to generate first and second light signals. The first and second light emitting elements may be electrically coupled to the first and second driver units.

Furthermore in accordance with an embodiment of the invention, the device further includes a dichroic beam-combiner, which may be configured to combine the first and second light signals into a single beam. The beam may include components of the first and second light wavelengths ($\lambda 1$ and $\lambda 2$) of the first and second modulation frequencies (F1 and F2), respectively.

Furthermore in accordance with an embodiment of the invention, the device further includes a reference detector configured to receive and measure a portion of the light incident on the dichroic beam-combiner.

Furthermore in accordance with an embodiment of the invention, the device further includes a detector-amplifier unit having light sensing means adapted to produce electric signals corresponding to the first and second light signals received by the detector-amplifier unit and to amplify the resulting electric signals; first and second synchronous detectors configured to receive the first and second signals and to extract the magnitude of the transmitted signal in wavelength $\lambda 1$ and frequency F1 and wavelength $\lambda 2$ and frequency F2 respectively, from the resulting electric signals.

Furthermore in accordance with an embodiment of the invention, the means for measuring the thickness includes one of a group of devices including a potentiometer, an optical measuring device, Rotary Variable Differential Transformer (RVDT) and a Linear Variable Differential Transformer (LVDT).

Furthermore in accordance with an embodiment of the invention, the device further includes gauging means for testing the device. The gauging means may include a testing jig composed of a transmissive material having known optical properties and thickness.

Furthermore in accordance with an embodiment of the invention, the device further includes means to eliminate external interference in the measured transmittance signals.

In addition, there is provided a method for measuring the bilirubin level of a subject. The method includes the steps of:
applying blanching pressure to the subject's living tissue;
determining the thickness of the subject's blanched tissue;
transmitting at least two different wavelengths through a subject's blanched tissue;
detecting and recording the signals transmitted through the tissue having blanching pressure applied thereto; and
calculating the bilirubin level in the subject using data obtained from the recorded signals and the thickness.

Furthermore in accordance with an embodiment of the invention, the method further comprises the step of gauging a device configured to measure the bilirubin level. Furthermore in accordance with an embodiment of the invention, the method further comprises the step of calculating first ($\lambda_0$) and second ($\lambda_1$) calibration constants.

Furthermore in accordance with an embodiment of the invention, the step of transmitting includes the step of configuring at least one radiation source for radiating the subject's living tissue.

Furthermore in accordance with an embodiment of the invention, the method further includes a gauging step, which includes the steps of:
transmitting at least two different wavelengths through a transmissive material having known optical properties and thickness;
detecting and recording the signals transmitted through the transmissive material and the signal of the thickness measuring means;
calculating the tissue transmittance at each wavelength, T ($\lambda$), according to the equation:

$$T(\lambda) = JT(\lambda)\frac{UT(\lambda)}{UJ(\lambda)}$$

wherein:
JT ($\lambda$) is the known transmittance of the transmissive material in a testing jig, at wavelength $\lambda$;
UT ($\lambda$) is the recorded detector signal in response to the light at wavelength $\lambda$ transmitted through the tissue; and
UJ ($\lambda$) is recorded detector signal in response to the light at wavelength $\lambda$ transmitted through the transmissive material; and
calculating the tissue thickness d, according to the equation:

$$d = Jd\frac{Ud}{UJd}$$

Wherein Jd is the known thickness of the transmissive material;
Ud is recorded signal of the thickness measuring means when the tissue is being measured; and
UJd is the recorded signal of the thickness measuring means when the testing jig is being measured.

Furthermore in accordance with an embodiment of the invention, the bilirubin level is calculated according to the equation:

$$B\hat{R} = A_0 + A_1 \frac{1}{d} \log_e \frac{T(\lambda 1)}{T(\lambda 2)}$$

wherein:
- $B\hat{R}$—calculated serum bilirubin level indication in mg/dl or μmol/L
- $A_0$—First calibration constant;
- $A_1$—Second calibration constant;
- d—The thickness of the measured tissue (e.g., in millimeters);
- $T(\lambda)$—The calculated transmittance of tissue for light of wavelength ($\lambda$).

Furthermore in accordance with an embodiment of the invention, the step of detecting the optical signals includes the step of removing ambient noise and interference from the received signal.

DESCRIPTION OF THE INVENTION

The present inventors have discovered that serum bilirubin levels in a living subject may be inferred from transcutaneous non-invasive measurements performed on the living tissue of a patient, by employing optical, electrical, and mechanical means in communication with processing means. Radiation is transmitted through the living tissue and measured by a detector or sensor. The thickness of the tissue is also measured. The processing means may be configured to calculate the serum bilirubin concentration based on the measured and detected values.

FIG. 1 illustrates a device 10 for measuring bilirubin levels according to one general preferred embodiment of the present invention. Device 10 comprises a housing 12 comprising processing means 12c in communication with a radiation source 12s, optical sensor means 12r, alert means 18 (optional), input means 19 for use by a human operator, and a display means 20. Radiation source 12s may be implemented by means of a white light emitter followed by two optical bandpass filters, two laser diodes, or two light emitting diodes, for example, capable of emitting radiation in two different wavelengths $\lambda 1$ and $\lambda 2$. By experimentation, it was found that the wavelengths giving the best results were 520 nm±5 nm and 470 nm±10 nm. However, persons knowledgeable in the art will appreciate that wavelengths outside these ranges may also be used to measure and achieve an indication of the bilirubin level.

Thus, the device may also comprise optical means (not shown) configured to direct beams of light emitted by light emitters from the radiation source 12s. Sensor 12r may also comprise optical coupling means (not shown) configured to direct beams of light to optical detectors comprised (not shown) therein.

In an alternative embodiment, the device may directly transmit and receive light without the need for light guiding means.

In an embodiment of the invention, device 10 may comprise tissue thickness measurement means, such as device comprising a pair of rotatable arms 14a and 14b, for example. The pair of rotatable arms 14a and 14b may comprise an elongated portion attached at one end to housing 12 by means of respective hinges 13a and 13b, and respective curved portions 14n at their free ends which are configured to define two contact surfaces 14m at the extremities of rotatable arms 14a and 14b, wherein contact surfaces 14m are facing each other in opposing relationship. Rotatable arms 14a and 14b are thus rotatable about their respective hinges 13a and 13b, and they further comprise respective light guiding means 5 and 6 passing along their lengths and along their curved portions 14n.

In another embodiment of the invention, the tissue thickness measurement means may comprise a clip or pincer device configured to be attached to the tissue being measured.

Light guiding means 5 may be adapted to deliver light emitted from radiation source 12s to an object 17 placed between the free extremities of rotatable arms 14a and 14b. Object 17 is either the tissue under test, or a test jig (not shown). The tissue being tested may be any tissue, such as the top of ear or ear lobe, for example, where the thickness of the tissue may be measured.

Light guiding means 6 may be adapted to collect light transmitted through the object 17 and deliver it to sensor means 12r. A first end 5i of light guiding means 5 emerging from the hinged end of movable arm 14a is adapted to receive light radiation emitted from radiation source 12s and deliver it to its other end 5f, which is aligned with contact surface 14m of rotatable arm 14a for emitting the light passed through it to the object 17. Light guiding means 6 may be adapted to collect light transmitted through the object 17 by a corresponding end 6f aligned with contact surface 14m of rotatable arm 14b such that light transmitted through the object is collected and passed therethrough and emitted via its other end 6j to optical detector means in sensor 12r. Light guiding means 5 and 6 may be implemented by means of any suitable fiber optics means, for example. The light radiation source may also be connected via other optical means to 14m and the sensor may also be connected via other optical means to the contact surface 14m.

In an alternative embodiment, the sensor may also be located close to the ear, without any need for transferring light.

Device 10 comprises input means 19 for operating the device. These input means may comprise buttons, switches and the like so that the operator can select the desired operating mode of the device and initiate its operation. The device may comprise two main modes: The "Gauging" mode and the "Measurement" mode.

In the measurement mode, processing means 12c, after receiving an appropriate activation command from the input means 19, sends a signal to the radiation source 12s to generate light in a first wavelength $\lambda 1$ (520 nm for example). The emitted light passes through light guiding means 5, which may be embedded in, or attached to the rotatable arm 14a. The light transferred through light guiding means 5 may be emitted at its distal end 5f, which may be aligned with contact surface 14m of rotatable arm 14a, and passes through object 17 (such as the top part of the ear, for example).

Light transmitted through 17 may be collected by light guiding means 6 aligned with surface 14m of rotatable arm 14b. The collected light is delivered through light guiding means 6 and emitted through its 6j to sensor means 12r, which measures the magnitude of light transmitted through tissue 17. The resulting signal may be sampled by the processing means and stored in its memory. The operation proceeds as processing means 12c sends another signal to the radiation source 12s to emit light radiation in a second wavelength $\lambda 2$ (470 nm, for example). The emitted light travels in the same path through light guiding means 5 to tissue 17 and to light guiding means 6, which collects light transmitted through tissue 17, and to sensor means 12r which measures the magnitude of light transmitted through tissue 17. The resulting signal may be sampled by the processing means and stored in its memory.

Additionally, the processing means may read and store the output of the thickness measuring means 12t (explained hereinafter).

In gauging mode, the same sequence occurs however, in this case object 17 is a test jig instead of tissue 17. The test jig may contain a transmissive material of known optical properties and thickness such as Neutral Density Filter, P63-385 (Edmund Optics).

The tissue transmittance at each wavelength, T(λ), is calculated by the processing means as the product of the known jig transmittance JT(λ) and the ratio of the tissue transmitted signal UT(λ) and jig transmitted signal UJ(λ), as shown in the following equation $$T(\lambda) = JT(\lambda)\frac{UT(\lambda)}{UJ(\lambda)} \quad (1)$$

The tissue thickness d is calculated by the processing means as the product of the known jig thickness, Jd, and the ratio of tissue net thickness signal Ud and the jig net thickness signal UJd in the following equation $$d = Jd\frac{Ud}{UJd} \quad (2)$$

The net thickness signal is the difference between the real thickness signal and a bias signal. The later is adjusted such that a zero d will be registered when object 17 is removed and the arms come into contact.

After calculating the thickness and transmittance of the tissue at the λ1 and λ2 wavelengths, processing means 12c calculates an estimate of the serum bilirubin level, as explained in the description hereinbelow. If the bilirubin level calculated by processing means 12c indicates high bilirubin levels (e.g., a level greater than a threshold value e.g. 12 mg/dl), then a corresponding indication may be issued by processing means 12c by sending a signal to visual and/or audible alert means 18 (such as a speaker or a beeper, for example), for alerting that the measured results indicate high chances of jaundice conditions in the subject. Power supply means (e.g., rechargeable batteries—not shown) are preferably provided for powering the electronic elements of device 10.

In an embodiment of the present invention, after calculating the bilirubin level, the processing means may send a signal to a digital display means for displaying the calculated result for the bilirubin level.

As seen in FIG. 1, spring 16, or any other suitable elastic element, may be used for mechanically coupling between rotatable arm 14a and 14b. Spring 16 is adapted to apply pressure over the tissue 17 maintained between rotatable arms 14a and 14b during the tissue measurements. Spring 16 is preferably configured to bring rotatable arms 14a and 14b together and apply pressure over tissue 17 such that the force that they apply over tissue 17 overcomes the systolic pressure, such that light transmitted through tissue 17 provide an indication of light transmittance through a piece of tissue from which blood has been expelled. This applied pressure is referred to herein as 'blanching pressure'. The blanching pressure is preferably larger than the systolic pressure.

Thickness measurement means 12t are preferably also provided in housing 12 for measuring the distance d between tips 14m of rotatable arms 14a and 14b. As exemplified in FIG. 1, thickness measurement means 12t may be implemented by means of a potentiometer or a Linear Variable Differential Transformer (LVDT), adapted for measuring the thickness (or width) d of the tested tissue 17. Processing means 12c is adapted to obtain tissue thickness d readings obtained by means of thickness measurement means 12t, which are then used for calculating the bilirubin levels in the tested tissue.

It will be appreciated by persons knowledgeable in the art, that thickness measurement means 12t may be implemented by any suitable means, such as by optical means, a potentiometer, an optical measuring device, Rotary Variable Differential Transformer (RVDT) and a Linear Variable Differential Transformer (LVDT).

In the preferred embodiment shown in FIG. 1, two rotatable arms 14a and 14b are used. In one specific preferred embodiment of the invention only one arm is made rotatable, while the other arm is fixedly attached to housing 12. However, having both arms 14a and 14b rotatable is advantageous since with this configuration movements and vibrations induced by the operator's hands while operating device 10 are substantially eliminated since both arms 14a and 14b are free to move relative to housing 12.

Figure 2:
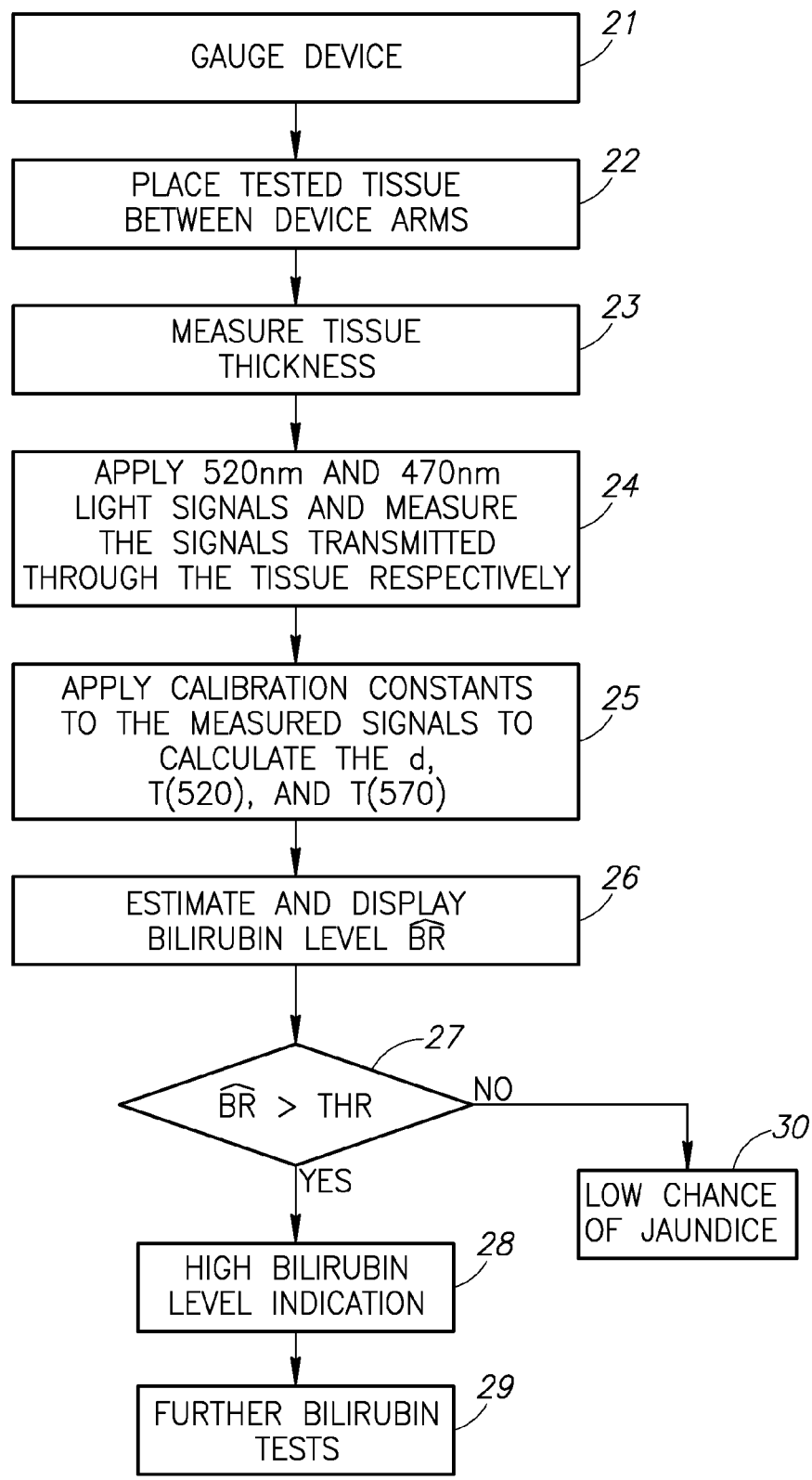
FIG. 2 is a flowchart illustrating a method for operating the device illustrated in FIG. 1.

The present invention furthermore provides a method for measuring the bilirubin levels in a living tissue. The method illustrated in block diagram shown in FIG. 2, is based on calculation of a bilirubin level indication by means of equation (3):

$$B\hat{R} = A_0 + A_1 \frac{1}{d}\log_e \frac{T(\lambda 1)}{T(\lambda 2)} \quad (3)$$

Wherein:
BR̂—calculated serum bilirubin level indication in mg/dl or μmol/L
$A_0$—First calibration constant;
$A_1$—Second calibration constant;
d—The thickness of the measured tissue (e.g., in millimeters);
T(λ)—The transmittance of tissue for light of wavelength (λ), calculated according to equation (1).

Equation (3) was developed following thorough research carried out by the inventors in which light transmittance and tissue thickness were measured in newborns that were scheduled for bilirubin measurement by means of the standard blood test. The first and second normalization constants were derived such that the differences between the true bilirubin levels and the calculated levels according to equation (3) were minimized in least square sense.

Reference is now made to FIG. 2, which is a flowchart illustrating a method for operating the device 10. The calibration constants $A_0$ and $A_1$ will have been stored in the device's memory in the factory during manufacture. The method may comprise a gauging step 21, performed at the manufacturing process or preferably on a regular basis, such as daily before commencing any measurements, for example. The gauging step comprises reading transmitted signals and thickness signal of the test jig and storing these in the memory of the processing means 12c for subsequent calculations.

In step 22, the tested tissue 17, such as the top part of the ear, for example, is placed between the device arms (14a and 14b). The arms are forced tightly as explained hereinabove to apply blanching pressure on tissue 17. The thickness signal of the pressed tissue is then measured and recorded in step 23, and in step 24 light signals are emitted in the two wavelengths (λ1 and λ2, such as 520 nm and 470 nm, for example). The measurements of the respective transmitted signals are carried out and recorded.

In step 25, the calibration constants are applied to the measured variables to calculate the tissue thickness and transmittance in the 520 nm and 470 nm wavelengths. In step 26 the estimated bilirubin level is calculated according to equation (3) and transferred to the display means 20.

Optionally, in step 27, it is checked whether the bilirubin level indication calculated in step 26 is above a predetermined level (Thr). Then in step 28, device 10 indicates that a high bilirubin level was measured (risk for jaundice conditions) in the subject, which may require further test as indicated in step 29. If it is determined in step 27 that the bilirubin level is below the predetermined level, then in step 30, device 10 indicates that low or normal bilirubin levels were measured.

In another embodiment of the invention d, T(λ1), and T(λ2) in equation (3) may be replaced with the signals Ud, UT(λ1) and UT(λ2). In this case, different normalization constants will replace $A_0$ and $A_1$ to reflect the change of the variables in equation (3).

According to one embodiment of the present invention, the bilirubin measurement device 10 generates the light beams of 520 nm and 470 nm concurrently, for a short period of time. The transmitted signals arrive simultaneously at the optical detector means where they are separated according to their wavelength, measured and stored. The operation of this embodiment proceeds with the calculations, display and alert via alert means 18 as described above.

Figure 3A:
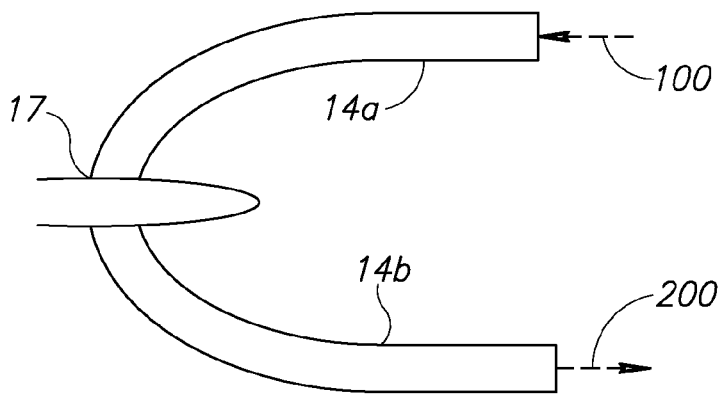
Figure 3B:
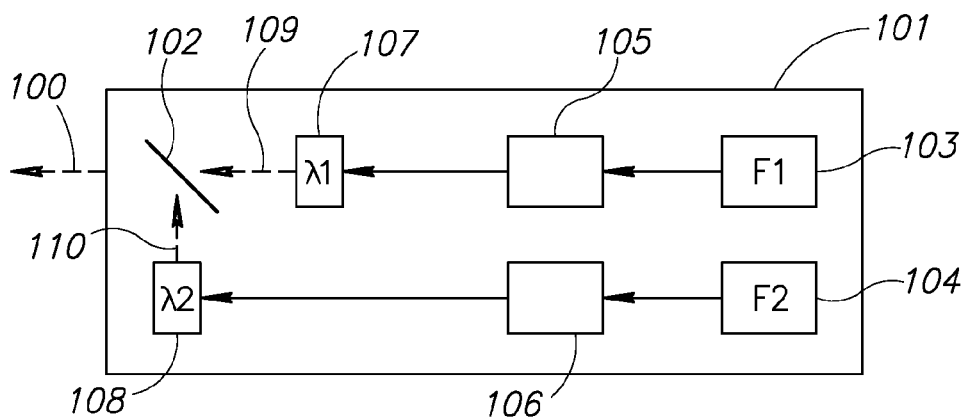
Figure 3C:
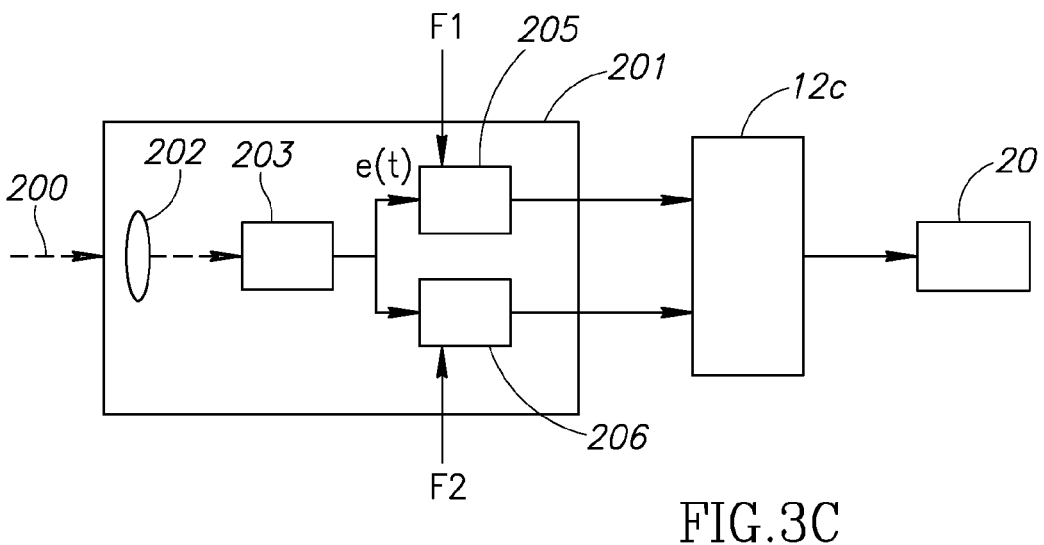

According to one embodiment of the present invention, the bilirubin measurement device is further adapted to eliminate external influences which may introduce noise and other such interferences in the measured transmittance signals (e.g., fluorescent light or any other such light source). FIGS. 3A to 3C illustrate one preferred embodiment for an implementation in which synchronous detection is used for substantially removing interfering light signals.

FIG. 3A provides a schematic illustration of light guiding arms 14a and 14b during transmittance measurements. A light beam 100 enters arm 14a, leaves arm 14a into the tested tissue 17. Transmitted light is collected by arm 14b and exit it as beam 200.

FIG. 3B is a block diagram showing one preferred embodiment of a radiation source 101 adapted for carrying out the synchronous detection technique of the invention. The radiation source 101 comprises two oscillators referenced at 103 and 104 which are configured to generate two different electrical signals having frequencies F1 and F2 respectively. Radiation source 101 further comprises two driver units 105 and 106 electrically coupled to oscillators 103 and 104, and two light emitting elements (such as light emitting diodes (LEDs), or laser diodes, for example) 107 and 108 adapted to generate light signals with center wavelengths λ1 and λ2 (such as, 520 nm and 470 nm, for example), which are electrically coupled to driver units 105 and 106. In this configuration, signals generated by oscillators 103 and 104 are used by driver units 105 and 106 as modulating signals for activating light emitting elements 107 and 108 such that they simultaneously produce light signals in the respective frequencies F1 and F2 produced by oscillators 103 and 104. Accordingly, in operation, light emitting elements 107 and 108 produce light signals 109 and 110 having F1 and F2 frequencies and λ1 and λ2 wavelengths, respectively.

As described above, in the present invention, the light beams to be transmitted through tissue 17 are in the 520 nm±5 nm and 470 nm±10 nm wavelength ranges and are modulated at frequencies F1 and F2 respectively. It should be noted that the F1 and F2 frequencies are predetermined frequencies. The emitted light signals 109 and 110 are coupled to a suitable beam combining means 102 (e.g., dichroic beam-combiner), which combines the light signals 109 and 110 into a single beam 100 comprising components of both light wavelengths (520 nm±5 nm and 470 nm±10 nm) and modulation frequencies (F1 and F2), respectively.

In an alternative embodiment, optional filters (not shown) may be inserted between the light emitting elements 107 and 108 and the beam combining means 102. In a further alternative embodiment, a reference detector (not shown) may be used to monitor the intensity of the beams generated by the light emitting elements 107 and 108. The reference detector receives a portion of the light incident on the beam combining means 102.

In an alternative embodiment, the light beams (for example blue and green) may be transmitted through tissue 17 at different times, instead of modulating the light beams by using different frequencies F1 and F2. In order to eliminate the ambient light, a measurement of the light is taken with the illuminating device switched off. The latter measured reading is taken after a pre-determined time period (after measuring the illuminated reading) and deducted from the illuminated reading to obtain the net illumination. The pre-determined time period may be determined by the nature of the ambient light.

With reference to FIG. 3C showing one embodiment of a detection unit 201, transmitted light beam 200 enters detection unit 201 wherein it is focused by optical means 202 (such as a lens, for example) and introduced into detector-amplifier unit 203. Detector-amplifier unit 203 comprises light sensing means adapted to produce electric signals corresponding to light signals received in detector/amplifier unit 203 and to amplify the resulting electric signals. The amplified signal e(t) produced by detector/amplifier unit 203 is fed into two synchronous detectors 205 and 206 which are also adapted to receive signals produced by oscillators 103 and 104 in the F1 and F2 frequencies, respectively. Synchronous detector 205 is adapted to extract from the electric signal e(t) the magnitude of the transmitted signal in wavelength λ1 and frequency F1. Synchronous detector 206 is adapted to extract from the electric signal e(t) the magnitude of the transmitted signal in wavelength λ2 and frequency F2. The output of the synchronous detectors 205 and 206 are then fed into processing means 12c.

Processing means 12c is adapted to sample the electric signals received and calculate the bilirubin level in accordance with equation (3), and display the calculated result value in display means 20, and issue alert indications, if so needed.

Figure 4A:
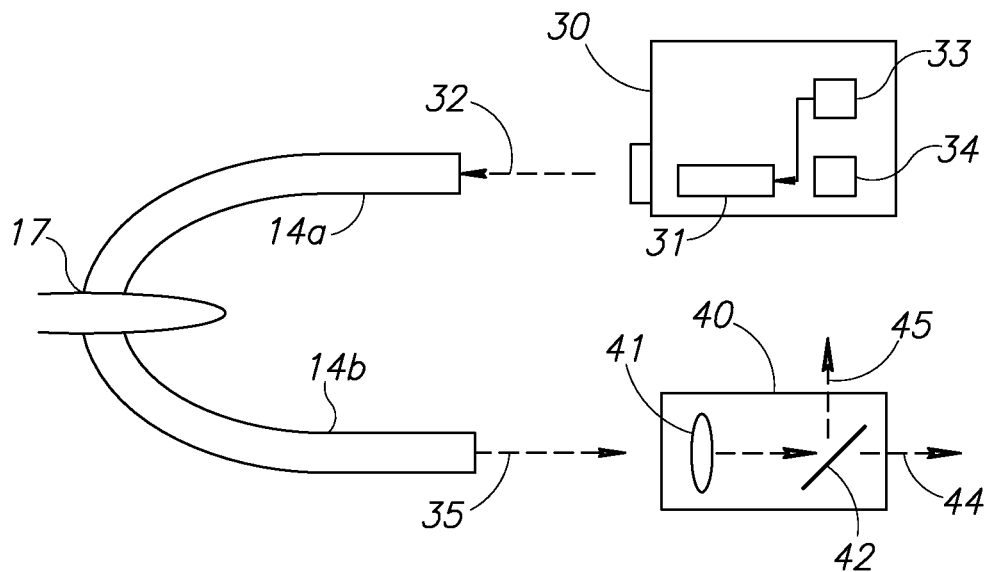
Figure 4B:
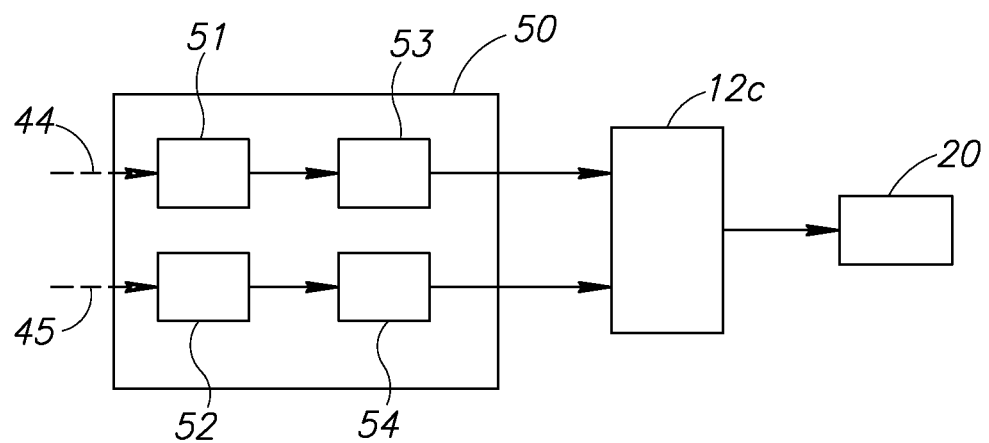

According to yet another embodiment of the invention, a flashtube may be employed as a light source, as shown in FIGS. 4A and 4B. The flashtube typically produces a short pulse of light radiation comprising a wide spectrum of wavelengths. Flashtube enclosure 30 comprises a flashtube 31, a power supply 34 to power the flashtube and a trigger unit 33 for activating flashtube 31 following a command from processing means 12c.

The flashtube 31 produces a pulsed light beam 32, which travels through arm 14a (through light guiding means 5), transmitted through tissue 17, collected and conducted through arm 14b, and emerges as light beam 35.

Light beam 35 enters optical unit 40 wherein it is focused by an optical means 41 (lens), and thereafter passed through a beam splitting means 42 (e.g., Dichroic beam splitter) which splits the light beam into two component beams: a transmitted beam 44 which includes the tissue transmitted light at wavelength λ1 (approx. 520 nm±5 nm) and a reflected beam 45 which includes the tissue-transmitted light at wavelength λ2 (approx. 470 nm).

With reference to FIG. 4B, light beams 44 and 45 enter electro-optic unit 50, which comprises two band-pass filter/detector units 51 and 52. The band-pass filter in unit 51 is adapted to pass the tissue-transmitted light at wavelength λ1 to the detector, while blocking all other spectral components of beam 44. The detector generates an electrical signal corresponding to the magnitude of tissue transmitted light at wavelength λ1. Likewise, the filter/detector unit 52 receives beam 45 and provides an electrical signal corresponding to the magnitude of tissue transmitted light at wavelength λ2. Peak detectors 53 and 54 sample and hold the peak values of the electrical signals generated by units 51 and 52. Processing means 12c converts these peak values to a digital format for the calculation of tissue transmittance at λ1 and λ2.

Processing means 12c calculates a bilirubin level indication according to equation (3) and provides the result value for display in display means 20.

Figure 5A:
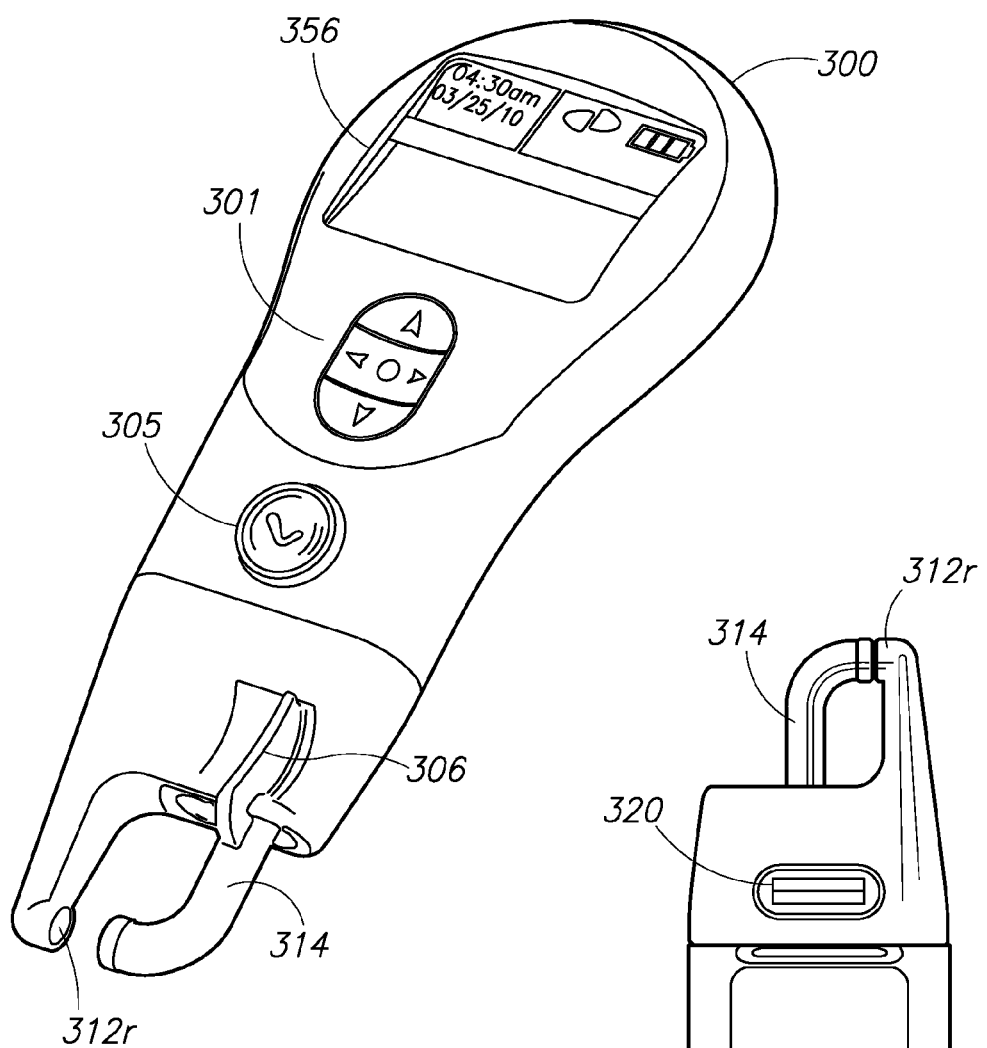
Figure 5B:
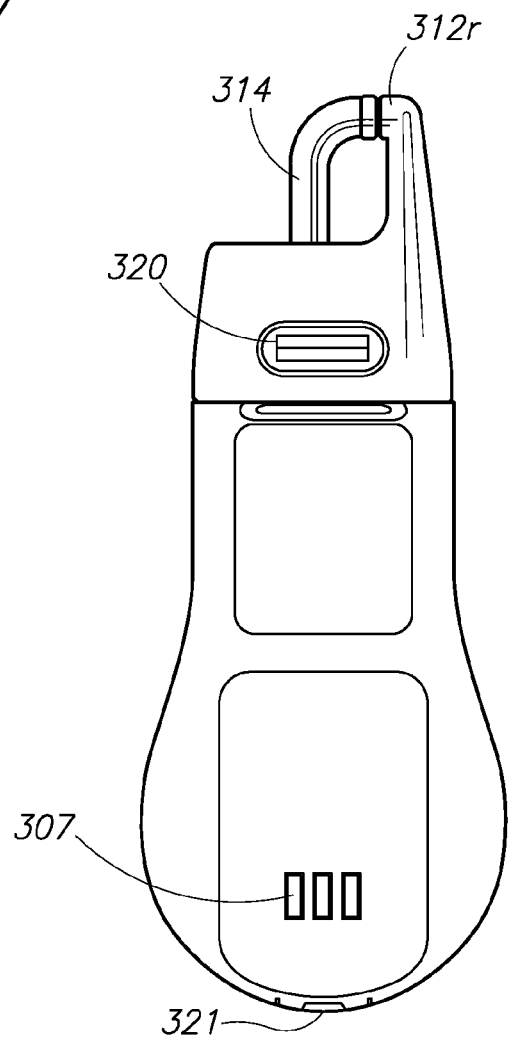

FIGS. 5A and 5B illustrate yet another embodiment of the present invention, showing a front perspective view and a rear view of device 300. Device 300 comprises the main elements of the embodiments explained above, (but not shown in FIG. 5). Device 300 further comprises operation buttons 301 for inputting device operation commands and activating button 305 for activating the device 300. Buttons 301 and 305 are possible embodiments of the input means 19.

Device 300 comprises a stationary arm 312r and a movable arm 314, with a force element holding them flush against each other such as a spring (not shown). The operator of the device 300 can engage lever 306 to open a gap between arms 312r and 314 such that the tissue 17, or test jig, can be placed in the gap. When lever 306 is released, the spring will apply the blanching pressure to expel the blood from the tissue that is between the arms. One arm conveys the illuminating light to the tissue, while the other arm receives light transmitted through the tissue and delivers it to the detection unit The thickness of the tissue d may be measured by means of a potentiometer or LVDT (not shown), or by any other thickness measuring element.

The processing means 12c (not shown) calculates a bilirubin level indication as explained hereinabove. A power source may be provided (not shown) for supplying power to all the elements in device 300. The power source is capable of being recharged by means of battery charging connectors 307. The display means 20 may be a display screen 356 provided for displaying the measured bilirubin level in a numerical format, or in a graphical format where the measured value is displayed as a point on nomogram, and for operation assistance.

Device 300 may comprise a barcode reader 320 for operation in a most efficient manner. Activation button 305 may activate the barcode reader 320 such that a patient's data is stored on board. After measuring the bilirubin level by device 300, the user can transfer the patient data along with the bilirubin level results to an external data processing system (e.g., personal computer, healthcare computer system, or the like) via data outlet 321. In this manner, a patient's bilirubin level can be measured and the results recorded on a central computer within a very short period of time. All this is performed in a non-invasive manner.

While some of the embodiments of the invention have been described by way of illustration, it will be apparent that the invention can be carried into practice with many modifications, variations and adaptations, and with the use of numerous equivalents or alternative solutions that are within the scope of a person skilled in the art, without departing from the spirit of the invention, or the scope of the claims.

The invention claimed is:

1. A non-invasive device for measuring the bilirubin level of a subject comprising:
   at least one radiation source for radiating a subject's living tissue, said at least one radiation source configured to emit radiation in at least first and second wavelengths;
   at least one detector for detecting rays transmitted through said tissue;
   means for applying blanching pressure to the portion of the subject's living tissue;
   means for measuring the thickness of the portion of the subject's living tissue through which radiation is being transmitted; and
   processing means in communication with said at least one radiation source, said at least one detector and said means for measuring thickness,
   wherein said processing means are configured to calculate the bilirubin level of said subject using data obtained from said at least one detector and from said thickness measurement means.

2. The device according to claim 1, wherein the means for applying blanching pressure comprise one of group of devices including a pair of rotatable arms, a single moving or rotating arm and a clip or pincer device, configured to be attached to the tissue being measured.

3. The device according to claim 1, wherein said at least first and second wavelengths comprise a first wavelength (λ1) within a range 520 nm±5 nm and a second wavelength (λ2) within a range 470 nm±10 nm.

4. The device according to claim 1, wherein said at least one radiation source comprises one of a group including at least two laser diodes, at least two light emitting diodes (or LEDs) and at least one laser diode together with at least one LED.

5. The device according to claim 4, wherein the device further comprises optical means configured to direct beams of light emitted from the at least one radiation source towards the subject's living tissue.

6. The device according to claim 5, wherein the light beams are transmitted through the tissue at different times.

7. The device according to claim 4, wherein the device further comprises light guiding means and optical coupling means, said optical coupling means configured to direct beams of light received from the light guiding means to said at least one detector.

8. The device according to claim 1, wherein said at least one radiation source comprises a white light emitter and at least two filters for filtering the emitted white light.

9. The device according to claim 1, wherein said at least one radiation source comprises means for emitting a synchronous signal, said synchronous signal comprising:
   first and second oscillators, configured to generate first and second electrical signals having first and second frequencies, respectively;
   first and second driver units electrically coupled to said first and second oscillators;
   first and second light emitting elements adapted to generate first and second light signals, said first and second light emitting elements electrically coupled to said first and second driver units.

10. The device according to claim 9, wherein the device further comprises:
    a dichroic beam-combiner, configured to combine said first and second light signals into a single beam, said beam comprising components of the first and second light wavelengths (λ1 and λ2) of the first and second modulation frequencies (F1 and F2), respectively.

11. The device according to claim 10, wherein the device further comprises:
a reference detector configured to receive and measure a portion of the light incident on the dichroic beam-combiner.

12. The device according to claim 9, wherein the device further comprises:
a detector-amplifier unit comprising light sensing means adapted to produce electric signals corresponding to said first and second light signals received by the detector-amplifier unit and to amplify the resulting electric signals;
first and second synchronous detectors configured to receive said first and second signals and to extract the magnitude of the transmitted signal in wavelength λ1 and frequency F1 and wavelength λ2 and frequency F2 respectively, from the resulting electric signals.

13. The device according to claim 1, wherein the means for measuring the tissue thickness comprises one of a group of devices including a potentiometer, an optical measuring device, Rotary Variable Differential Transformer (RVDT) and a Linear Variable Differential Transformer (LVDT).

14. The device according to claim 1, further comprising gauging means for testing the device.

15. The device according to claim 14, wherein the gauging means comprises a testing jig composed of a transmissive material having known optical properties and thickness.

16. The device according to claim 1, further comprising means to eliminate external interference in the measured transmitted signals.

17. A method for measuring the bilirubin level of a subject comprising the steps of:
applying blanching pressure to the subject's living tissue;
determining the thickness of the subject's blanched tissue;
transmitting at least two different wavelengths through a subject's blanched tissue;
detecting and recording the signals transmitted through the tissue having blanching pressure applied thereto; and
calculating the bilirubin level in the subject using data obtained from said recorded signals and said thickness.

18. The method according to claim 17, further comprising the steps of:
gauging a device configured to measure the bilirubin level; and
calculating first (A0) and second (A1) calibration constants.

19. The method according to claim 18, further comprising a gauging step, said gauging step comprising the steps of:
transmitting at least two different wavelengths through a transmissive material having known optical properties and thickness;
detecting and recording the signals transmitted through the transmissive material and the signal of the thickness measuring means;
calculating the tissue transmittance at each wavelength, $T(\lambda)$, according to the equation:

$$T(\lambda) = JT(\lambda)\frac{UT(\lambda)}{UJ(\lambda)}$$

wherein:
$JT(\lambda)$ is the known transmittance of the transmissive material in a testing jig, at wavelength $\lambda$;
$UT(\lambda)$ is the recorded detector signal in response to the light at wavelength $\lambda$ transmitted through the tissue; and
$UJ(\lambda)$ is recorded detector signal in response to the light at wavelength $\lambda$ transmitted through the transmissive material; and
calculating the tissue thickness d, according to the equation:

$$d = Jd\frac{Ud}{UJd}$$

Wherein, Jd is the known thickness of the transmissive material;
Ud is recorded signal of the thickness measuring means when the tissue is being measured; and
UJd is the recorded signal of the thickness measuring means when the testing jig is being measured.

20. The method according to claim 18, wherein the step of calculating the bilirubin level is calculated according to the equation:

$$B\hat{R} = A_0 + A_1\frac{1}{d}\log_e\frac{T(\lambda 1)}{T(\lambda 2)}$$

wherein:
$B\hat{R}$—calculated serum bilirubin level indication in mg/dl or μmol/L
$A_0$—First calibration constant;
$A_1$—Second calibration constant;
d—The thickness of the measured tissue (e.g., in millimeters);
$T(\lambda)$—The calculated transmittance of tissue for light of wavelength ($\lambda$).

21. The method according to claim 17, wherein the step of transmitting comprises the step of:
configuring at least one radiation source for radiating the subject's living tissue.

22. The method according to claim 17, wherein said step of detecting comprises the step of
removing ambient noise and interference from the received signal noise and interference from the ambient light.

* * * * *